United States Patent [19]

Merrill et al.

[11] Patent Number: 5,125,890
[45] Date of Patent: Jun. 30, 1992

[54] VACUUM-CONSTRICTION ERECTION AID DEVICE

[75] Inventors: Daniel C. Merrill, Walnut Creek; William B. Andersen, Antioch, both of Calif.

[73] Assignee: Bak Medical Products, Martinez, Calif.

[21] Appl. No.: 724,473

[22] Filed: Jun. 28, 1991

Related U.S. Application Data

[63] Continuation-in-part of Ser. No. 659,235, Feb. 22, 1991, abandoned.

[51] Int. Cl.⁵ .............................. A61F 5/00
[52] U.S. Cl. ........................................ 600/39
[58] Field of Search ........................... 128/79

[56] References Cited

U.S. PATENT DOCUMENTS

| | | | |
|---|---|---|---|
| 1,399,095 | 12/1921 | Webb, Sr. | 128/79 |
| 2,874,698 | 3/1959 | Sell | 128/79 |
| 4,378,008 | 3/1983 | Osbon, Sr. | 128/79 |
| 4,741,329 | 5/1988 | Marcune | 128/79 |
| 4,753,227 | 6/1988 | Yanuck, Jr. | 128/79 |
| 4,856,498 | 8/1989 | Osbon | 128/79 |
| 4,856,499 | 8/1989 | Kelly | 128/79 |
| 5,020,522 | 6/1991 | Stewart | 128/79 |

FOREIGN PATENT DOCUMENTS 347300  8/1960  Switzerland ........................ 128/79

OTHER PUBLICATIONS

Witherington R. Suction Device—Therapy in the Management of Erectile Impotence, Urol. Clinics North Am. 15:123 (1988).
VED Vacuum Constriction Device—Mission Pharmacal Co., P.O. Box 1676, San Antonio, Tex.
Osbon Erecaid Erection Inducer—Osbon Medical Systems Ltd., 1253 Broad St., P.O. Box 1478, Augusta, Ga.
E.I.D. Erection Inducer Device—Performance Medical, Cherry Hill, N.J.

*Primary Examiner*—Cary E. O'Connor

[57] ABSTRACT

To simplify and increase the efficacy of tubular vacuum chamber (6) used to induce and maintain erections in impotent men, a penile sealing diaphragm (7) forms an airtight seal between the tubular chamber (6) and the penis (28). A constriction band dislodging mechanism comprising a flexible strap (36) which is attached to the sealing diaphragm (7) provides a simple method for transferring any constriction band (8) from the chamber (6) onto the penis (28). A constriction band dislodging-vacuum release mechanism is used to simultaneously dislodge a constriction band (8) and relieve the vacuum within a chamber with an air hole (38). A unique constriction band (44) is formed from an inexpensive rubber band and two strips of glass tape which is easy to dislodge from the vacuum chamber (8) and easy to remove from the penis (28).

28 Claims, 3 Drawing Sheets

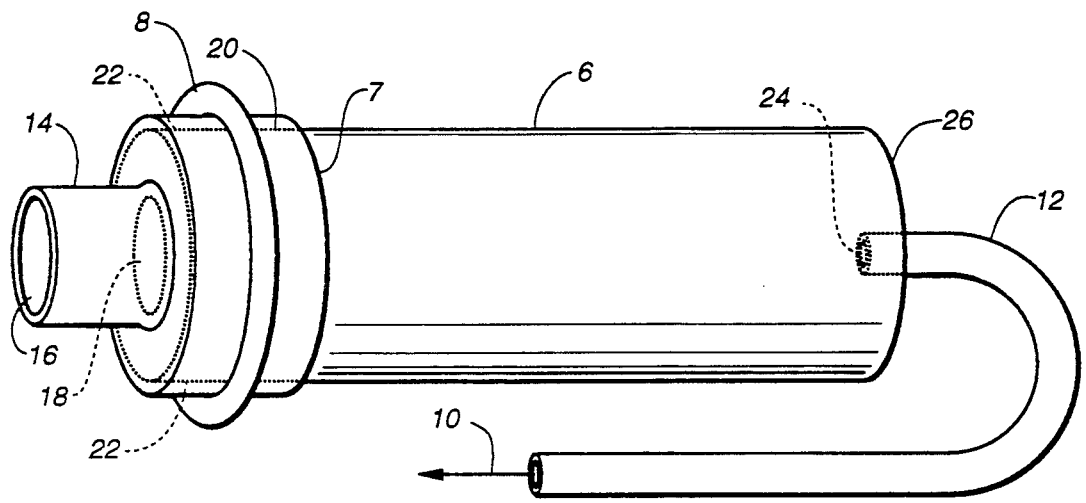
FIG._1
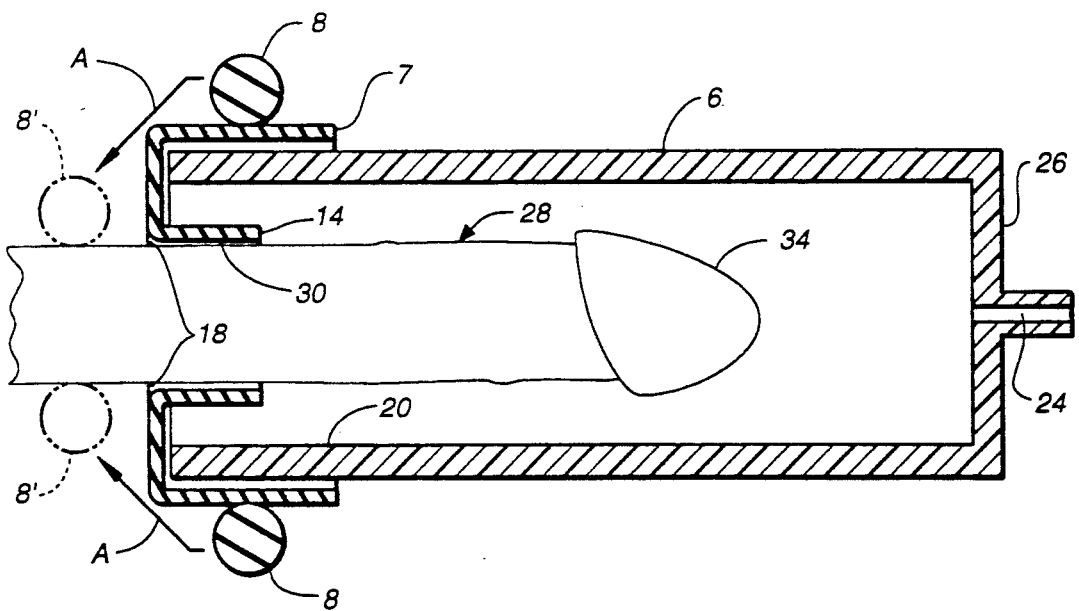
FIG._2

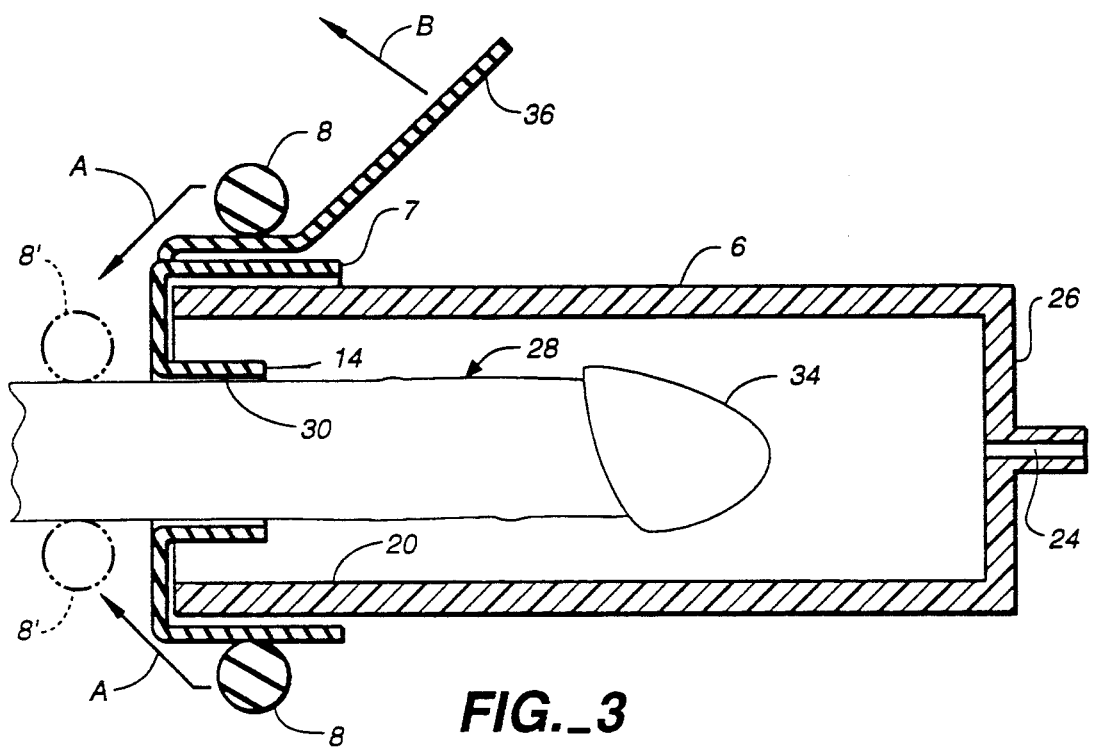
FIG._3
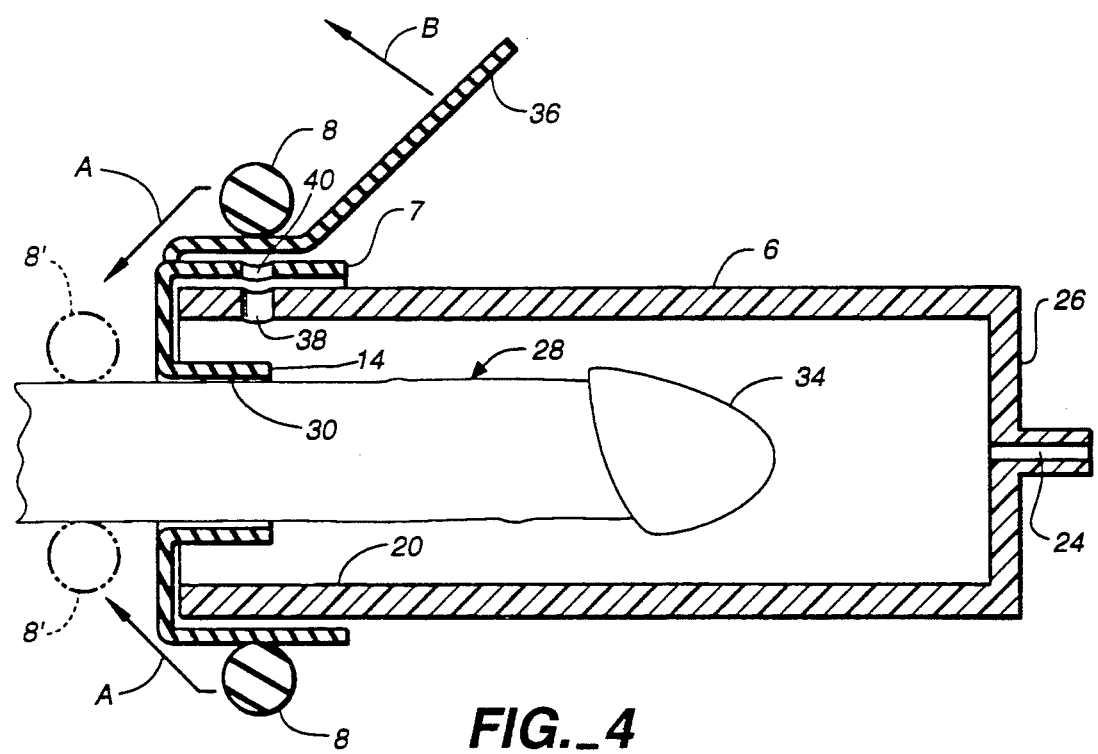
FIG._4

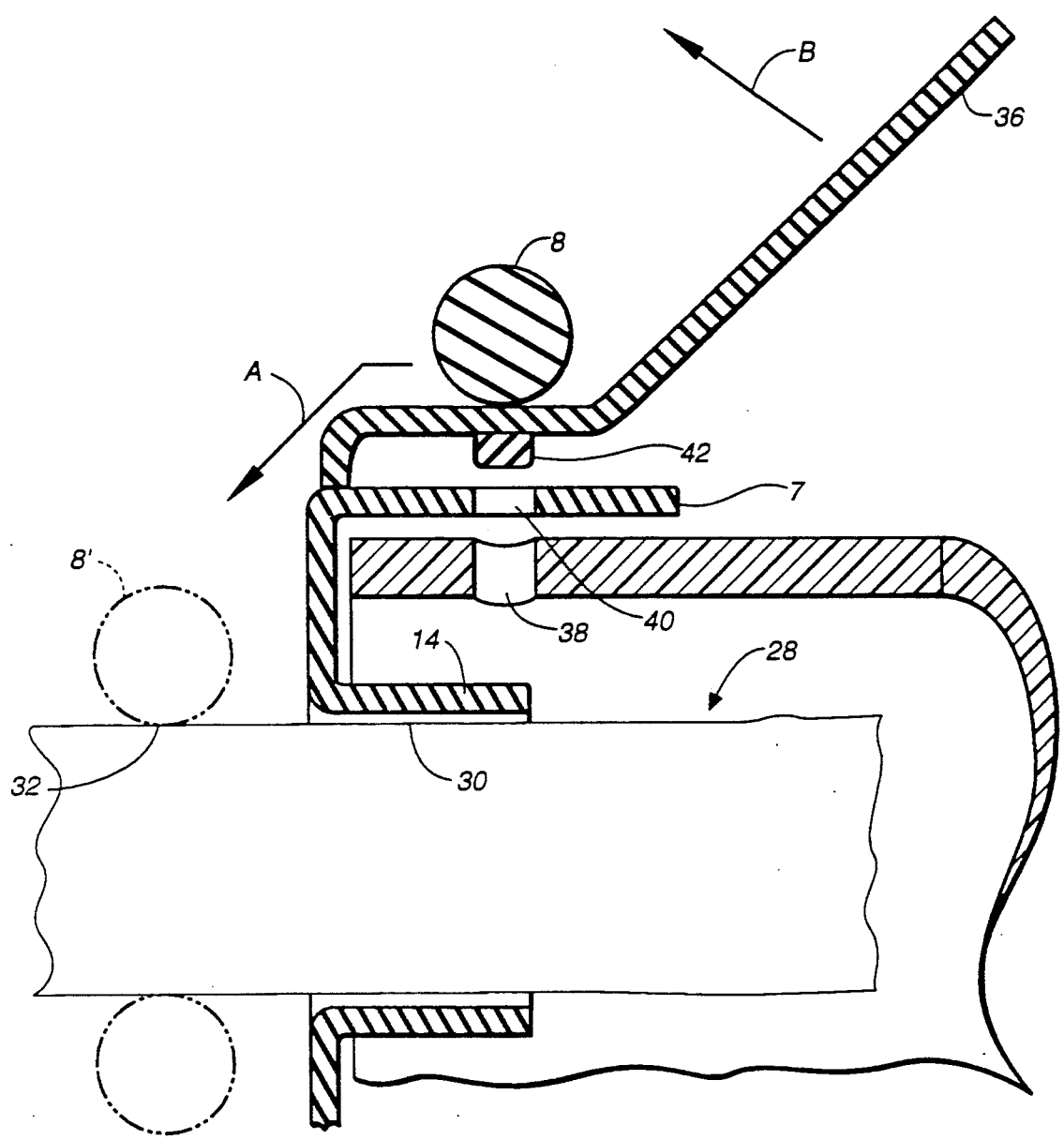
FIG._4A
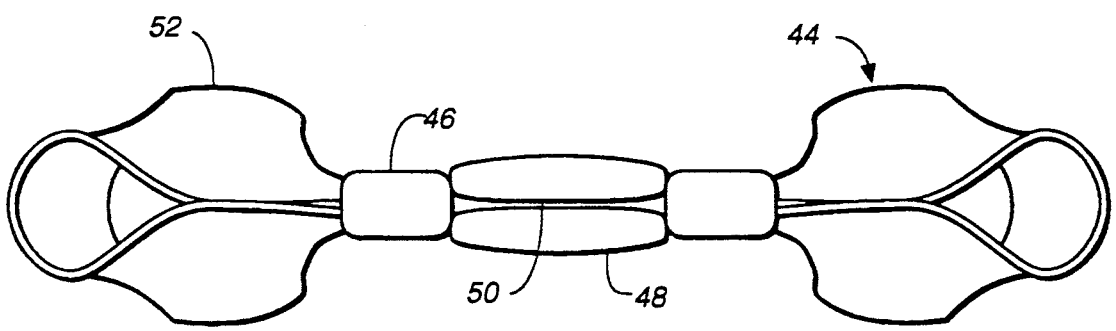
FIG._5

VACUUM-CONSTRICTION ERECTION AID DEVICE

CROSS-REFERENCE TO RELATED APPLICATION

This is a continuation-in-part of Ser. No. 07/659,235, filed Feb. 22, 1991, now abandoned.

BACKGROUND

1. Field of Invention

This invention relates to erection aids, specifically to vacuum-constriction erection aid devices used to induce and maintain erections in impotent males.

2. Description of Prior Art

Impotence is a common medical problem affecting over 10,000,000 American males. In the past, psychological impotence was treated primarily by sex therapy while organic (physical) impotence usually was treated by injection therapy or implantation of a penile prosthesis. All of these treatment modalities have major disadvantages. Sex therapy is costly, time consuming, and often ineffective; injection therapy is painful and may induce scarring of the erectile bodies; and penile implants require costly surgical procedures which may result in serious complications. Vacuum-constriction therapy provides an attractive alternative to these standard treatment options because it is a noninvasive, painless, and relatively inexpensive procedure which produces immediate results and can be used in all types of impotence.

Vacuum-constriction therapy employs erection aid devices which produce a partial vacuum around the penis. This vacuum expands the blood vessels in the penis which in turn increases blood flow to the organ and causes it to become erect. After an erection has been achieved, an elastic constriction band is placed around the base of the penis to impede blood flow from the organ and maintain the erection. Prior developments in this field will be generally illustrated by reference to the following patents, publications, and commercial products:

| Patent No. | Patentee | Issue Date |
|---|---|---|
| 347,300 | Giuseppe Meldi (Italy) | 02/22/57 |
| 2,874,698 | F. W. Sell | 03/24/59 |
| 4,378,008 | Gedding D. Osbon, Sr. | 03/29/83 |
| 4,741,329 | Benjamin F. Marcune | 05/03/88 |
| 4,753,227 | Rudolph R. Yanuck, Jr. | 06/28/88 |

Witherington R. Suction Device—Therapy in the Management of Erectile Impotence Urol. Clinics North Am. 15:123(1988).

VED TM Vacuum Constriction Device—Mission Pharmacal Co., P.O. Box 1676, San Antonio, Tex.

Osbon ERECAID SYSTEM TM Erection Inducer—Osbon Medical Systems Ltd., 1253 Broad Street, P.O. Box 1478, Augusta, Ga.

E.I.D. TM Erection Inducer Device—Performance Medical, Berlin, N.J.

All of these vacuum-constriction devices, except meldi's, have four essential components—a cylindrical penile vacuum chamber, a vacuum pump, a vacuum release valve, and a constricting elastic band (Osbon patent, supra). There have been numerous modifications of these devices since Dr. Otto Lederer described the first erection aid device in 1917 (Witherington R., supra). A comprehensive review of these is beyond the scope of this discussion, so only those listed above, which relate to our invention, will be reviewed herein.

To achieve a partial vacuum around the penis, the open end of a penile vacuum chamber must make an airtight seal with the penis or the abdominal wall around the penis. Devices which form a junction with the abdominal wall surrounding the penis (Marcune patent, supra) may suck the skin and testicles into the vacuum chamber, causing inconvenience, pain, and injury. Devices which form a seal with the penis require adapter inserts (Osbon ERECAID TM, supra) to decrease the diameter of the chamber's opening. The adapter inserts are inconvenient to use and may make it difficult to remove the device from the erect penis.

Meldi shows an erection aid device with a penile sealing diaphragm. Meldi's device increases the effectiveness of erection aids designed solely to induce an erection because it makes a tight seal with the penis rather than the abdominal wall. Meldi's erection aid, however, is not a true vacuum-constriction device because it does not have the elastic constriction band which most impotent men require to maintain the erection generated within a vacuum chamber. There are two other significant disadvantages to Meldi's device. First, Meldi's penile sealing diaphragm is designed for use with a vacuum chamber which has a lip of rim to fix the diaphragm to the vacuum chamber. The diaphragm would easily slip off of a chamber which did not have a flanged end. The need for such an attaching means greatly decreases the versatility and applicability of Meldi's device since modern vacuum chambers do not have protruding lips of rims to which the diaphragm could be attached. Present-day vacuum chambers have smooth walls because any protrusion on their distal wall would interfere with band transfer from the chamber to the penis. Second, Meldi's diaphragm is a complex device having a very irregular shape. Because of its complexity, Meldi's diaphragm can not be made from a simple segment of rubber tubing, rather it must be formed by a molding process, a manufacturing technique which greatly increases the cost of producing the device.

Prior-art vacuum-constriction devices also are difficult to operate because the operator must use his fingers to push the constriction band off of the penile vacuum cylinder onto the penis. Recognition of this problem resulted in the development of erection aid devices with an outer sleeve which can be pushed or pulled toward the abdomen to dislodge the constriction band from the penile vacuum chamber to the penis (Sell patent, supra; Yanuck patent, supra). While these devices may facilitate transfer of the constriction band to the penis, their construction entails complicated mechanical alterations of the penile vacuum chamber which are costly to manufacture.

Another disadvantage of prior-art vacuum erectors is the need to perform two separate and distinct functions, to transfer the constriction band from the vacuum chamber to the penis and to relieve the vacuum within the chamber. The sequence of these functions, which may be confusing to elderly males most in need of the device, is important because the erection may be lost if the vacuum is released before the constriction band has been transferred. To obviate these disadvantages Yanuck also shows a vacuum release valve which opens automatically when a sleeve is activated to transfer the constriction band to the penis. This mechanism facilitates the use of erection aid devices, but is complicated and costly to manufacture.

Finally, the constriction bands used to maintain the erection induced in a penile vacuum chamber are expensive to manufacture, difficult to dislodge from the penile vacuum chamber, and difficult to remove from the penis. Strings have been looped around the constriction bands to facilitate their removal from the penis (rubber bands with safety loops, VED TM Vacuum Constriction device, supra). Constriction bands also have been made with side loops (Osbon ERECAID TM, supra) or tabs (E.I.D. TM Erection Inducer Device, supra) which may be used to pull the bands from the penis. However, such strings easily become tangled in the pubic hair and the loops and tabs are difficult to use because they stretch and become more difficult to grasp when they encircle the erect penis.

The constriction bands also must apply differing degrees of tension to the penis to accommodate variations in penile anatomy. The tension applied by the bands has been increased by doubling the bands (Osbon ERECAID TM supra), but this makes them extremely difficult to apply to the vacuum chambers and equally difficult to remove from the penis. Variations in band tension also have been achieved by varying the elasticity of the rubber used to manufacture the bands (E.I.D. TM Erection Inducer Device, supra), a method which increases the complexity and expense of manufacturing the bands. Also, doubling the bands may create excessive constrictive forces, which may cause gangrene.

OBJECTS AND ADVANTAGES

Accordingly, several objects and advantages of our invention are to provide an improved penile erection device which is easy to use, reliable and inexpensive to manufacture. Other objects are to provide such a device which:

a) forms an airtight seal between modern smooth-walled penile vacuum chambers and the penis;

b) provides a simple method for dislodging a constriction band from a penile vacuum chamber onto the penis;

c) provides a simple, inexpensive means to simultaneously dislodge a constriction band from a penile vacuum chamber and relieve the vacuum in the chamber; and d) provides a unique constriction band which can be manufactured from simple, inexpensive components.

Further objects and advantages of our invention will become apparent from a consideration of the drawings and ensuing description.

BRIEF DESCRIPTION OF THE DRAWINGS:

FIG. 1 is a pictorial view of a vacuum-constriction device according to our invention showing a penile sealing diaphragm.

FIG. 2 is a sectional perspective view of the vacuum-constriction device of FIG. 1 applied to a penis showing how the penile sealing diaphragm makes an airtight seal between the open end of a penile vacuum chamber and the penis.

FIG. 3 is a sectional perspective view of an erect aid device according to another embodiment of our invention showing a dislodging strap which may be used to transfere a constriction band from a vacuum chamber to the penis.

FIG. 4 is a sectional perspective view of a vacuum-constriction device according to another embodiment of our invention which has means for dislodging a constriction band from a penile vacuum chamber and releasing the vacuum in the chamber simultaneously.

FIG. 4A is a fragmentary sectional perspective view of the vacuum-constriction device shown in FIG. 4 which has an air hole sealing plug attached to the undersurface of the constriction band dislodging strap.

FIG. 5 is a pictorial view of a constriction band formed from a rubber band and two strips of glass tape; this band may be used in the devices of FIGS. 1, 2, 3, 4, and 4A or with other prior-art erection aid devices.

DRAWING REFERENCE NUMERALS:

6 penile vacuum chamber
7 penile sealing diaphragm
8 constriction band
10 vacuum source
12 connecting tube
14 penile sealing sleeve
16 distal opening in penile sleeve
18 proximal opening in penile sleeve
20 distal wall of penile vacuum chamber
22 open end of penile vacuum chamber
24 inlet orifice
26 closed end of penile vacuum chamber
28 penis
30 proximal penile shaft
32 root of penis
34 glans penis
36 constriction band dislodging strap
38 air hole in penile vacuum chamber
40 air hole in penile sealing diaphragm
42 air hole sealing plug
44 specific constriction band
46 glass tape
48 central penile constricting segment
50 lumen of central constricting segment
52 finger loop

DESCRIPTION—ERECTION AID DEVICE WITH PENILE SEALING DIAPHRAGM, FIGS. 1 AND 2

Such terms as "upward" and "downward" and "left" and "right" refer to the device as illustrated in the drawing, not to their position in actual use, which is indeterminate.

FIG. 1 shows an erection aid device in accordance with the invention. It consists of a penile vacuum chamber 6, a penile sealing diaphragm 7, a constriction band 8, and a flexible tube 12 which communicates with a source of vacuum indicated by arrow 10. Diaphragm 7 is formed from a segment of thin walled elastic tubing (not shown) approximately 7.5 cm long, 2.5 cm in diameter, and having a wall thickness of approximately 0.1 cm. To form penile sealing diaphragm 7, approximately 2.5 cm of the material of diaphragm 7 is stretched and placed over distal wall 20 of vacuum chamber 6 to cover the chamber's open end. Diaphragm 7 is shown separated from chamber 6 to facilitate illustration, but in actuality diaphragm 7 will be tightly pressed to chamber 6 in all figures. The remaining unstretched tubing segment forms a penile sealing sleeve 14 with a distal opening 16 and a proximal opening 18. An elastic constriction band 8 encircles distal wall 20 of chamber 6. Note that chamber 6 has no lip, rim, or other means for attaching diaphragm 7 to the chamber. Therefore, the segment of tubing which covers the distal wall of chamber 6 must be long enough to firmly grip the chamber's wall so that the diaphragm will not become detached from the chamber during use.

An inlet orifice 24 or nipple is situated on closed end 26 of chamber 6. A flexible tube 12 connects orifice 24 of chamber 6 to a source of vacuum (not shown). A suitable vacuum source may be a hand-operated vacuum pump, such as used in the ERECAID ™, supra, or an electronically operated pump which produces a vacuum of about 175 mm of mercury.

FIG. 2 shows a chamber 6 installed over a penis 28. Sealing sleeve 14 has been inverted into the chamber so that it forms a seal with the proximal end of penile shaft 30. Although sleeve 14 is shown separated from penis 28 to facilitate illustration, in actuality sleeve 14 is tightly pressed to penis 28 in all figures. After an erection has been generated, band 8 is dislodged from the distal wall of chamber 6 onto the root of penis 32 as indicated by arrows A and by the phantom band 8'.

OPERATION OF THIS EMBODIMENT

The device is used to create an erection in an impotent male as follows: penile sealing sleeve 14 is inverted into chamber 6 as shown in FIG. 2. A surgical lubricant, such as that sold under the mark SURGILUBE, manufactured by E. Fougera & Co., Melville, N. Y., is applied to the inner and outer surfaces of sleeve 14, the inner surface of chamber 6, and penis 28. The vacuum pump (not shown) is activated and glans penis 34 is introduced into proximal opening 18 of sleeve 14. The partial vacuum generated in chamber 6 sucks penis 28 further into the chamber, until penile sealing diaphragm 7 reaches the abdominal wall (not shown) and sealing sleeve 14 surrounds the proximal part of penile shaft 30. The partial vacuum is maintained until an erection is achieved, which usually occurs in about 3 minutes. After an erection has been achieved, band 8 is dislodged from chamber 6 to position 8' on the root of penis 32 by the user's fingers (not shown). Referring to FIG. 1, the vacuum is relieved by disconnecting tube 12 from orifice 24 prior to removing chamber 6 from penis 28. At the completion of intercourse, band 8' is removed from penis 28.

Use of this embodiment eliminates the need for expensive adapter rings since the penile sealing sleeve stretches to accommodate penises of varying girth. The penile sealing diaphragm prevents suction of the testicles and scrotal skin into the penile vacuum chamber when a partial vacuum is generated within the chamber. The sealing diaphragm also increases the success of vacuum-constrictor therapy because its sealing penile sleeve provides a more reliable airtight seal than do devices which form a seal with the abdominal wall. Furthermore, since the diaphragm makes a seal with the penis, shaving or cutting the hair around the penis is not necessary as it is with erection aid devices which form a seal with the abdominal wall. Because the elastic tube from which sealing diaphragm 7 is constructed is long enough to cover a significant portion of the vacuum chamber's distal wall, the diaphragm grips the chamber's wall and will not slip off of the chamber during use. Thus our penile sealing diaphragm may be used with modern vacuum chambers which do not have lips or rims to fix the diaphragm to the chamber's wall. This design feature is important because a penile sealing diaphragm such as Meldi's, supra, would slip off of a modern smooth-walled vacuum chamber during use.

DESCRIPTION—ERECTION AID DEVICE WITH ELASTIC BAND DISLODGING MEMBER, FIG. 3

FIG. 3 shows another embodiment of the erection aid device according to the invention. Here diaphragm 7 has a constriction band dislodging strap 36. Strap 36 is shown separated from diaphragm 7 for illustration; in actuality the proximal end of strap 36 is tightly pressed against diaphragm 7 by band 8 in all figures. Strap 36 is formed from a portion of flat flexible, but mimimally stretchable, material, such as latex rubber, approximately 2.0–4.0 cm wide, 4.0–6.0 cm long and 0.15 cm thick. One end of the strap is attached by a suitable adhesive, such as that sold under the mark LOCTITE SUPER BONDER, manufactured by Loctite Corporation, Newington, Conn., to diaphragm 7 at the point where it crosses the open end of the chamber. Band 8 is positioned over strap 36 so that an upward pull on strap 36 pushes band 8 off the distal wall of chamber 6 onto the root of penis 32, as indicated by arrows A.

OPERATION OF THIS EMBODIMENT

Before insertion of penis 28 into chamber 6 band 8 is placed over dislodging strap 36 where the strap crosses distal wall 20 of chamber 6. After an erection has been generated in chamber 6, strap 36 is pulled upward, as shown by arrow B, to dislodge band 8 from the chamber onto the root of penis 32.

Use of this embodiment of the invention simplifies the use of erection aid devices since it provides a simple method for the user to transfer an elastic band from a penile vacuum chamber to the penis. Our band transfer mechanism also is easier and cheaper to manufacture than are the prior-art devices (Sell patent, supra; Yanuck patent, supra) which utilize a sleeve to push the constriction band off of the chamber onto the penis.

DESCRIPTION—ERECTION AID DEVICE WITH BAND DISLODGING AND VACUUM RELEASE MECHANISMS, FIG. 4

FIG. 4 shows still another embodiment. This device is formed from vacuum chamber 6 which has an air hole 38 in its wall adjacent to its distal (left) end. Penile sealing diaphragm 7 has an air hole 40 and a constriction band dislodging strap 36. Diaphragm 7 is positioned over the open end of chamber 22 so that air hole 40 overlies air hole 38. The proximal portion of strap 36 is placed over air hole 40 in diaphragm 7 so that it forms an airtight seal with air holes 40 and 38. Band 8 is positioned over the portion of the strap which covers air hole 40. An upward pull on strap 36 dislodges band 8 and uncovers air holes 40 and 38 to allow atmospheric air to enter chamber 6 and release the vacuum as indicated by the arrows A and by phantom band 8'.

OPERATION OF THIS EMBODIMENT

To use this device, airholes 40 and 38 are covered by strap 36 to prevent air entering chamber 6. Band 8 is placed over strap 36 to hold strap 36 over airholes 40 and 38 while a partial vacuum is being developed around penis 28. After a penile erection has been generated within chamber 6, strap 36 is pulled upward, as indicated by arrow B, to dislodge band 8 from the chamber. As strap 36 is pulled upward, airholes 40 and 38 are uncovered, allowing atmospheric air to enter chamber 6 and relieve the vacuum. Thus, with one movement of the user's hand, the vacuum within chamber 6 is relieved and band 8 is transferred from the chamber to penis 28, as indicated by arrows A and phantom band 8'.

The use of this embodiment greatly simplifies vacuum-constriction therapy because the elastic band is transferred from the vacuum chamber to the penis and the vacuum is relieved in the chamber simultaneously with one movement of the user's hand. The effectiveness and success of vacuum therapy also is increased by this mechanism since it is impossible for the user to release the vacuum within the chamber, and by so doing lose his erection, before the constriction band has been transferred to this penis. The vacuum constriction system described by Yanuck (Yanuck patent, supra) also provides a mechanism for simultaneous band transfer and vacuum release; however, this device is much more complicated and expensive to manufacture.

DESCRIPTION—BAND TRANSFER VACUUM RELEASE DEVICE WITH AIR HOLE SEALING PLUG, FIG. 4A

FIG. 4A shows a modification of the erection aid device shown in FIG. 4. An airhole sealing the plug has been attached to the undersurface of strap 36 so that plug 42 may enter and seal air holes 40 and 38. Band 8 is positioned over strap 36 and plug 42 to hold the plug firmly in air holes 40 and 38 while a partial vacuum is being generated in chamber 6.

OPERATION OF THIS EMBODIMENT

After a partial vacuum has been generated in chamber 6. an upward pull on strap 36 draws plug 42 from air holes 40 and 38 to relieve the vacuum in chamber 6 while simultaneously dislodging band 8 from the distal wall of the chamber onto the penis, as indicated by the arrow A and by phantom band 8'.

This embodiment of our device increases the reliability of the band transfer vacuum release device because the presence of the air hole sealing plug on the undersurface of the band dislodging strap assures that an airtight seal is made between the strap and the vacuum chamber. This mechanism is different from the one described by Yanuck (Yanuck patent, supra) since the strap and sealing plug are held firmly in position by the overlying elastic band whereas Yanuck's device relies on a sleeve to hold the vacuum release value and sealing plug in the vacuum chamber air hole.

DESCRIPTION—SPECIFIC CONSTRICTION BAND, FIG. 5

The devices described above are designed to function with any prior-art constriction band. FIG. 5 shows a specific constriction band 44 of our invention that has been formed from a rubber band 12-16 cm in length, 1.0-2.0 cm in width, and having a wall thickness of approximately 0.15 cm. Two 1.25×7.5 cm strips of glass tape (not shown) have been wrapped tightly around the rubber band to divide the band into a central penile constricting segment 48 and two lateral finger loops 52. To prevent movement of the strips 46 when lumen 50 of segment 48 is stretched, the rubber band is stretched to a length of approximately 30 cm before the glass tape strips are applied to it. The length of central segment 48, defined by the distance between the strips of glass tape, determines the tension developed in the walls of the constricting segment when it encircles the penis (not shown). Thus, constricting segments 48 of varying tensions may be formed from the same size rubber bands by varying the distance between the strips of glass tape. Depending on the elasticity of the rubber band, its dimensions, and the tension desired in its central segment, the length of unstretched central segment 48 of band 44 may vary between 1.5 and 3.0 cm.

The segments of tape strips 46 also form dislodging bosses when they are wrapped around the rubber band. The dislodging bosses may be used to push band 44 off chamber 6 onto the penis. Finger loops 52 are used to pull constricting segment 48 from the penis following intercourse. Because finger loops 52 are separated from constricting segment 48 by tape strips 46, the finger loops do not change configuration when central segment 48 is stretched over the penis.

OPERATION OF SPECIFIC CONSTRICTION BAND

To operate band 44, two fingers of each hand are introduced into its central lumen 50. The lumen is stretched and positioned over the distal wall of penile vacuum chamber 6 as shown in FIG. 1. Surgical lubricant is placed on the central constricting segment to facilitate its removal from chamber 6. After an erection has been generated in chamber 6, the user's fingers are used to push glass tape dislodging bosses 46, and band 44, from chamber 6 onto the penis. If the erection aid device has a dislodging strap 36, as shown in FIGS. 3 and 4, the strap is used to dislodge band 44 from chamber 6. Following intercourse, the penis is lubricated again and finger loops 52 are used to pull band 44 from the penis.

There are several advantages to our constriction band. The band may be manufactured from a simple, inexpensive rubber band and two strips of glass tape. The tension of the constriction band's control segment may be altered simply by varying the distance between the tapes when they are applied to the rubber band. The glass tape strips also form dislodging bosses which facilitate transfer of the band from the penile vacuum chamber to the penis while the finger loops provide an easy way to remove the band from the penis.

SUMMARY, RAMIFICATIONS, AND SCOPE

Thus, the reader will see that there are many advantages to the various embodiments of our invention. Our penile sealing diaphragm forms an airtight seal with normal sized penises of varying girth and eliminates the need for adapter rings. Since the seal is made with the penis, rather than the abdominal wall, shaving or cutting of the hair around the penis is not necessary as it is with erection aid devices which do not have a penile sealing diaphragm. The sealing diaphragm also prevents suction of the scrotal skin and testicles into the chamber when a vacuum is generated within the chamber. The penile sealing diaphragm may be used with modern vacuum chambers because it does not require a lip or rim to fix the diaphragm to the chamber. Such a protrusion would impede the transfer of an elastic band from the chamber to the penis.

Our constriction band dislodging strap provides a simple way to transfer the constriction band from the penile vacuum chamber to the penis and eliminates the frustration men experience pushing the bands off of the vacuum chamber. Our air holed penile vacuum chamber provides a way to simultaneously dislodge the constriction band and release the vacuum within the penile vacuum chamber preventing premature release of the vacuum and loss of the erection before the constriction band has been transferred to the penis. Our constriction bands have dislodging bosses which facilitate their transfer to the penis and finger rings which make it easy to remove the bands from the penis. Finally, the embodiments of our invention are simple and inexpensive to manufacture, which will reduce the cost of vacuum-constriction therapy.

While our above description contains many specificities, these should not be considered as limitations of the scope of the invention, but rather as amplifications of preferred embodiments thereof. Many other variations are possible.

For example, the penile sealing diaphragm may be molded so that the diameter of the segment that is positioned over the end of the penile vacuum chamber is larger than the diameter of the segment which forms the penile sleeve. This design makes it easier to place the diaphragm over the open end of the penile vacuum chamber. The wall thickness of the middle and ends of the sealing diaphragm also may be different to make it easier to stretch the end which is placed over the cylinder. The end of the diaphragm's sleeve also may be serrated to increase the effectiveness of the seal which is achieved with the penis.

The constriction band dislodging strap may be formed from a nylon filament, such as heavy fishing line, rather than from a flexible strap. Alternately, the dislodging member can be formed from inflexible material such as plastic. The dislodging member can be attached to the open end of any penile vacuum chamber or to a cylinder adapter ring, rather than to the penile sealing diaphragm we have shown in our preferred embodiment. Similarly, an erection aid device can be formed with more than one constriction band dislodging member, rather than the single strap we have used in our illustrations.

It also will be apparent to the reader that our constriction bands can be formed from rubber bands of varying lengths, widths, and wall thicknesses. Similarly, round bands of elastic material similar to "O-rings" may be used to form the constriction bands. Rubber bands or tapes of different colors can be used to identify differing tension constriction bands. Similarly, segments of heat-shrunk tubing, manufactured by California Terminal Products, El Cajon, CA, of differing colors may be placed over the glass tape strips to identify bands with differing tension.

Thus the scope of the invention should be determined by the appended claims and their legal equivalents, rather than by the examples given.

We claim:

1. A device for inducing and sustaining an erection of a penis, comprising:
   a) an elongated tubular penile vacuum chamber with a closed end and an open end receptive of said penis,
   b) means connected to said closed end of said tubular penile vacuum chamber to remove air from said chamber to induce blood flow to said penis so as to cause said erection,
   c) elastic tube means for achieving an airtight seal between said open end of said penile vacuum chamber and said penis,
   d) elastic band means for constricting the blood flow from said penis, said band being manufactured from a rubber band and two strips of inelastic material,
   e) elastic band dislodging means for transferring said elastic band from said penile vacuum chamber to said penis, said dislodging means being formed from a member which has been attached to said elastic tube means, and
   f) vacuum release means for simultaneously relieving said vacuum in said chamber while said band is transferred from said chamber onto said penis.

2. The device recited in claim 1 wherein said elastic tube means is formed from a segment of elastic tube, one end of said tube being stretched to cover said open end of said penile vacuum chamber, the other end of said elastic tube forming an elastic sleeve which will achieve said airtight seal with said penises of varying girth.

3. The device recited in claim 2 wherein said elastic tube is approximately 7.5 cm in length, 2.5 cm in diameter and has a wall thickness of about 0.1 cm.

4. The device recited in claim 1 wherein said rubber band is approximately 12 to 16 cm in length, 1.0 to 2.0 cm in width, and has a wall thickness of about 0.15 to 0.2 cm.

5. The device recited in claim 1 wherein said two strips of inelastic material divide said band into the following three segments, a central segment and two lateral segments, the distance between said strips determining the tension said central segment applies to said penis, said lateral segments forming loops which facilitate removal of said band from said penis.

6. The device recited in claim 5 wherein said two strips of inelastic material are formed from two strips of glass tape, each of which is approximately 7.5 cm long and 1.25 cm wide.

7. The device recited in claim 1 wherein said elastic band dislodging means is formed from a piece of flexible flat material.

8. The device recited in claim 7 wherein said piece of flexible flat material is formed from a piece of latex rubber approximately 1.5 to 3.0 cm wide, 4.0 to 6.0 cm long, and 0.2 cm thick.

9. The device recited in claim 1 wherein said chamber and said elastic band dislodging means have air holes, said air holes being covered by an air hole sealing plug which has been attached to the undersurface of said elastic band dislodging means.

10. A device for inducing and sustaining an erection of a penis, comprising:
    a) an elongated tubular penile vacuum chamber with a closed end and an open end receptive of said penis, said open end of said chamber being smooth and free of any obstructions which will impede the transfer of an elastic band from over said chamber onto said penis,
    b) means connected to said closed end of said penile vacuum chamber for removing air from said chamber to induce blood flow to said penis so as to cause said erection,
    c) elastic tube means for achieving an airtight seal between said open end of said penile vacuum chamber and said penis,
    d) elastic band means for constricting blood flow from said penis, said elastic band means being positioned over said penile vacuum chamber, and
    e) elastic band dislodging means for transferring said elastic band from said penile vacuum chamber onto said penis, said dislodging means comprising a member which has been attached to said elastic tube means.

11. The device recited in claim 10 wherein said elastic tube means comprises a segment of elastic tube, about 2.5 cm of one end of said tube being stretched to cover about 2 to 3 cm of said chamber's distal wall, the other end of said elastic tube forming an elastic sleeve which will achieve said airtight seal with said penises of varying girth.

12. The device recited in claim 11 wherein said segment of elastic tube is approximately 7.5 cm in length, 2.5 cm in diameter, and has a wall thickness of about 0.1 cm.

13. The device recited in claim 10 wherein said elastic band dislodging means is formed from a piece of flexible flat material.

14. The device recited in claim 13 wherein said piece of flexible flat material is formed from a segment of latex rubber approximately 1.5 to 3.0 cm wide, 4.0 to 6.0 cm long, and about 0.15 cm thick.

15. The device recited in claim 10 wherein said elastic band means is manufactured from a rubber band and two strips of inelastic material.

16. The device recited in claim 15 wherein said rubber band is approximately 12 to 16 cm in length, 1.0 to 2.0 cm in width, and has a wall thickness of about 0.1 to 0.2 cm.

17. The device recited in claim 15 wherein said two strips of inelastic material divide said rubber band into three segments, namely, a central segment and two lateral segments, the distance between said strips determining the tension said central segment applies to said penis, said lateral segments forming finger loops which facilitate removal of said band from said penis.

18. The device recited in claim 10 wherein said vacuum chamber and said elastic tube means have air holes, said air holes being covered by said elastic band dislodging means.

19. The device recited in claim 18 wherein said air holes are covered by an air hole sealing plug which has been attached to the undersurface of said elastic band dislodging means.

20. An erection aid device, comprising:
a) an elongated tubular penile vacuum chamber with a closed end and an open end receptive of a penis, said chamber being smooth and free of any obstructions which may impede the transfer of an elastic band from over said chamber onto said penis, said chamber having an air hole,
b) means connected to said closed end of said penile vacuum chamber to remove air from said chamber to create a partial vacuum in said chamber to increase blood flow to said penis so as to cause said erection of said penis,
c) elastic tube means for achieving an airtight seal between said open end of said penile vacuum chamber and said penis, said elastic tube having an air hole which overlies said air hole in said penile vacuum chamber,
d) elastic band means for constricting the blood flow from said penis,
e) elastic band dislodging means for transferring said elastic band means from said penile vacuum chamber to said penis, said dislodging means being formed from a member which has been attached to said elastic tube means, and
f) vacuum release means for simultaneously relieving the vacuum in said chamber when said elastic band dislodging means is activated to transfer said elastic band from said chamber onto said penis.

21. The device recite in claim 20 wherein said elastic tube means is formed from a segment of elastic tube, one end of said tube being stretched to cover said chamber's open end and said chamber's distal wall, said elastic tube's other end forming an elastic sleeve which will achieve said airtight seal with said penises of varying girth.

22. The device recited in claim 21 wherein said elastic tube is approximately 7.5 cm in length, 2.5 cm in diameter, and has a wall thickness of about 0.1 cm.

23. The device recited in claim 20 wherein said elastic band dislodging means is formed from a piece of flexible flat material.

24. The device recited in claim 23 wherein said piece of flexible flat material is formed from a segment of latex rubber approximately 1.5 to 3.0 cm wide, 4.0 to 6.0 cm long, and about 0.15 cm thick.

25. The device recited in claim 20 wherein said elastic band means is manufactured from a rubber band and two strips of inelastic material.

26. The device recited in claim 25 wherein said rubber band is approximately 12 to 16 cm in length, 1.0 to 2.0 cm in width, and has a wall thickness of about 0.15 to 0.2 cm.

27. The device recited in claim 25 wherein said two strips of inelastic material divide said rubber band into the following three segments, namely, a central segment and two lateral segments, the distance between said strips determining the tension said central segment applies to said penis, said lateral segments forming loops which facilitate removal of said band from said penis.

28. The device recited in claim 20 wherein an air hole sealing plug is attached to the undersurface of said elastic band dislodging means, said plug being held firmly in said air holes of said vacuum chamber and said elastic tube means by said elastic band means, said plug being pulled from said holes to relieve said partial vacuum in said chamber when said elastic band dislodging means is activated to transfer said elastic band from said chamber to said penis.

* * * * *